US005536301A

United States Patent [19]
Lansbarkis et al.

[11] Patent Number: 5,536,301
[45] Date of Patent: Jul. 16, 1996

[54] METHODS FOR ANALYSIS OF VOLATILE ORGANIC COMPOUNDS IN WATER AND AIR

[75] Inventors: James R. Lansbarkis, El Dorado; Jon S. Gingrich, Sacramento; Catherine L. Lindberg, Folsom, all of Calif.

[73] Assignee: UOP, Des Plaines, Ill.

[21] Appl. No.: 411,097

[22] Filed: Mar. 27, 1995

[51] Int. Cl.$^6$ ................................................ B01D 53/04
[52] U.S. Cl. .......................... 95/117; 95/123; 95/126; 95/141; 95/143; 95/147
[58] Field of Search .......................... 95/117–120, 123, 95/141, 143–148

[56] References Cited

U.S. PATENT DOCUMENTS

| | | | |
|---|---|---|---|
| 3,702,886 | 11/1972 | Argauer et al. | 423/328 |
| 3,960,520 | 6/1976 | Allen | 95/147 X |
| 4,003,257 | 1/1977 | Fletcher et al. | 95/141 X |
| 4,061,724 | 12/1977 | Grose et al. | 423/335 |
| 4,257,885 | 3/1981 | Grose et al. | 210/691 |
| 4,309,281 | 1/1982 | Dessau | 95/143 X |
| 4,663,052 | 5/1987 | Sherman et al. | 95/117 X |
| 4,836,911 | 6/1989 | Skeels et al. | 208/111 |
| 5,012,037 | 4/1991 | Doshi et al. | 95/147 X |
| 5,256,173 | 10/1993 | Rastelli | 95/141 |
| 5,271,914 | 12/1993 | Sugimoto et al. | 95/141 |
| 5,281,257 | 1/1994 | Harris | 95/147 X |
| 5,346,535 | 9/1994 | Kuznicki et al. | 95/141 X |
| 5,425,242 | 6/1995 | Dunne et al. | 95/119 X |

FOREIGN PATENT DOCUMENTS 0586830  3/1994  European Pat. Off. ............ 95/117

*Primary Examiner*—Robert Spitzer
*Attorney, Agent, or Firm*—Thomas K. McBride; Eugene I. Snyder

[57] ABSTRACT

The purge and trap procedure commonly used for analysis of volatile organic compounds in water or air can be significantly improved using traps employing molecular sieves as adsorbents. Silicalite and potassium-exchanged dealuminated zeolite Y form an effective mixture.

22 Claims, No Drawings

METHODS FOR ANALYSIS OF VOLATILE ORGANIC COMPOUNDS IN WATER AND AIR

BACKGROUND OF THE INVENTION

With the heightened environmental concern regarding the presence of contaminants in drinking water has come the need to analyze water for volatile organic compounds generally. The purge and trap technique is a general purpose method for the identification and simultaneous measurement of purgable, volatile organic compounds in water that have sufficiently high volatility and sufficiently low water solubility to be efficiently removed from water. Among the volatile organic compounds which can be determined by the purge and trap procedure are benzene, bromobenzene, carbon tetrachloride, chloroform, cumene, naphthalene, styrene, toluene, the xylenes, vinyl chloride, tetrachloroethylene, hexachlorobutadiene, methylene dichloride and fluorodichloromethane. An analogous technique also is used for the analysis of volatile organic compounds in air.

In a typical purge and trap procedure, exemplified by EPA Method 524.2, volatile organic compounds and surrogates with low water solubility are purged (extracted) from the sample by bubbling an inert gas through the aqueous sample. Purged sample components are trapped in a tube containing suitable sorbent materials. When purging is complete, the sorbent tube is heated and backflushed with helium to desorb the trapped sample components into a capillary gas chromatography (GC) column interfaced to a mass spectrometer (MS). The column is temperature programmed to separate the analytes which are then detected with the MS. Compounds eluting from the GC column are identified by comparing their measured mass spectra and retention times to reference spectra and retention times in a database. Reference spectra and retention times for analytes are obtained by the measurement of calibration standards under the same conditions used for samples. A concentration of each identified component is measured by relating the MS response of the quantitation ion produced by that compound to the MS response of the quantitation ion produced by a compound that is used as an internal standard. Surrogate analytes, whose concentrations are known in every sample, are measured with the same internal standard calibration procedure.

The foregoing description was that for analysis of volatile organic materials in aqueous systems where the purge and trap technique is appropriate. However, it should be clear that an analogous procedure may be utilized for the analysis of volatile organic materials in, e.g., air analysis. The exposition within will be directed with particularity to analysis of volatile organics in aqueous media using the purge and trap procedure, but this is done solely for clarity and ease of exposition. It needs to be clearly understood that the subject matter is not restricted to such analyses, and is capable of significant expansion.

This application focuses on the sorbent tubes used in purge and trap analysis. In particular, our goal is the development of an improved sample concentration sorbent tube, superior to those presently available, to enhance the purge and trap procedure itself, both as to its methodology and its results.

The jet separator specified in, for example, EPA Method 524.2 for analysis using a GC/MS system can cause losses of 50% or more for small analytes, a condition alleviated somewhat by interfacing the column directly to a MS ion source. Elimination of the jet separator requires low column flow rates, which are not compatible with flow rates in purge and trap systems. Another option for improving sensitivity is the use of larger samples. Since both these options have significant disadvantages, we turned our attention to finding a sorbent tube considerably more efficient than those currently used.

Present adsorbents in the sorbent tubes used for purge and trap methodology appear to be one or more of various charcoals or porous carbons, organic polymers such as that of 2,6-diphenylene oxide (e.g., Tenax®), and silica gels. Each individually and even in combination suffer from distinct limitations and disadvantages. One disadvantage is that of limited capacity, so that "saturation" of the adsorbent is all too readily attained, leading to error in analytic results. Each also suffers from a lack of thermal stability, with temperatures of 200° C. or so likely to lead to irreversible impairment as an adsorbent. Each additionally suffers from hysteresis or "memory" effects, i.e., complete desorption of some components may be difficult with additional desorption occurring during subsequent analyses using the same sorbent tube in a different purge cycle. This is frequently referred to as "carryover."

Perhaps the most severe limitation of present materials commonly used as adsorbents in purge and trap methods is their very limited linearity. That is, the adsorbents typically utilized by those in the art discriminate among the various classes of organic materials which may be present, and also may discriminate among the organic materials within a class. Thus, a substantial proportion of analysis time must be spent in calibrating sorbent tubes for their nonlinearity. What is instead desired are adsorbents which are linear, or nearly so, with respect to the adsorption, storage and desorption of a broad spectrum of organic components over a wide dynamic concentration range. Although all of the foregoing limitations of present adsorbents have been noted, despite the long-felt need for improved sorbent tubes none have been forthcoming.

Although our invention is simple, it is an extraordinarily effective solution to the foregoing problems and fills a commercial void which has existed for more than a decade. What we have found is that when the sorbent tubes of the purge and trap unit use certain molecular sieves as adsorbents one can very effectively and efficiently adsorb volatile and semi-volatile organic compounds found in contaminated water. Furthermore, the capacity of these molecular sieves as adsorbents in sorbent tubes mandated for use by the EPA is sufficient that "breakthrough" through saturation by components at high concentrations is rarely a threat. Complete desorption of all components is readily attained with avoidance of hysteresis effects because one can utilize substantially higher desorption and bakeout temperatures than are available to the prior art sorbent tube materials; one need not worry about analytical errors arising from materials remaining in a sorbent tube from prior analyses. The resulting benefit is better run-to-run reproducibility and a higher precision in measurement evidenced by a lower relative standard error of deviation. Another benefit is longer sorbent tube lifetime. That is, our adsorbents can undergo more adsorb-desorb cycles than those in the sorbent tubes presently in commercial use. But perhaps most important of all is that the sorbent tubes of this invention exhibit linearity in absorption, linearity in storage, and linearity in desorption, and exhibit such linearity over a dynamic range which easily spans four orders of magnitude. Thus calibration becomes an infrequent occurrence. These cumulative benefits are substantial, and offer advantages over the prior art sorbent tubes which are advantages in kind rather than advantages in degree.

SUMMARY OF THE INVENTION

The purpose of this invention is to make possible the analysis of volatile organic compounds in water or air by a purge and trap procedure using as an adsorbent material which shows linearity in adsorption, storage, and desorption of the organic compounds over a wide dynamic concentration range, with a high capacity, and little or no hysteresis. An embodiment comprises utilizing as a trap in classical purge-and-trap procedures an adsorbent which is a molecular sieve, or combination of sieves. In a specific embodiment the sieve is a highly siliceous molecular sieve, with a silicon to aluminum framework atom ratio of at least 20:1. In another embodiment the molecular sieve is a cation-exchanged, dealuminated zeolite L or zeolite Y. In a still more specific embodiment the cation is potassium.

DESCRIPTION OF THE INVENTION

Our invention relates to the deployment of well-known materials as adsorbents in a particular field of use. Although the materials themselves have been recognized as adsorbents in many applications, they have not been used for the purge and trap procedures used in the analysis of organic compounds present in water and in air. In particular, although there has been a long felt need to supplant the adsorbents currently used in purge and trap procedures, nonetheless the need has remained unmet. More specifically, even though analysis of trace organic components in aqueous streams by a combination of gas chromatography and mass spectrometry has for some time suffered from the limitations of, e.g., silica, porous carbon, and organic polymers as adsorbents, no substitutes have been commercially offered. We now describe an improvement which is at once simple and extraordinarily effective, for it makes possible a procedure with enhanced linearity, greater reproducibility and precision, decreased carryover adversely affecting analytical accuracy, less frequent calibration, and longer operational material lifetime.

Our improvement to current purge and trap procedures is the employment of molecular sieves as adsorbents to replace, partially or preferably totally, the current adsorbents. Perhaps the most outstanding feature of the molecular sieves of this invention as adsorbents compared to the current state of the art is their linearity. That is, our adsorbents adsorb, store and desorb a wide range of organic species in proportionately equal amounts; there is a one-to-one correspondence between the incoming organic species and the desorbed species. This linearity is independent of the mix of organic materials up to the adsorbent saturation point, and linearity is maintained over a dynamic range of better than $10^4$, often from 0.5 ppb up to 100 ppm, with linearity over this range better than 0.1%. In comparison, current sorbent tube materials, such as silica gel, carbon in its various forms, and organic polymers such as polyethers, exhibit variable linearity depending upon the batch of material used, the thermal history of the adsorbent, and the mixture of the adsorbed species. In part the current commercial materials exhibit nonlinearity because their structures may change with temperature cycling, whereas the materials of our invention are quite stable to temperature cycling.

An associated benefit of the high thermal stability of our materials is that one can employ both a high desorption temperature and an even higher bakeout temperature. High desorption temperatures tend to promote a linear response and also promote short desorption times, thereby reducing analysis time. Because the desorption temperature is inversely proportional to the concentration of material remaining on the adsorbent, a high bakeout temperature tends to minimize memory and hysteresis effects; bakeout at, e.g., 400° C. tends to remove all adsorbed species from the sorbent tube, and in a reasonably short time.

The adsorbents which are used in our improved sorbent tubes are molecular sieves, i.e., crystalline zeolitic material having a three-dimensional framework in which generally a combination of $Al^{3+}$ and $Si^{4+}$ are in tetrahedral coordination with 4 oxygens in the framework, and where all of the oxygens in the tetrahedra are mutually shared between the tetrahedral silicon or aluminum atoms. It needs to be noted that there are molecular sieves which contain little or no $Si^{4+}$, as well as molecular sieves which contain little or no $Al^{3+}$. There also are molecular sieves where $Al^{3+}$ is tetrahedrally coordinated in the framework with other charge balancing elements, such as phosphorus. The assemblage of linked tetrahedral units leads to discrete channels with a well-defined size and shape within the crystalline material arising from secondary building units, i.e., the framework topology. One type of adsorbent advantageously used in the practice of our invention consists of molecular sieves having relatively high ratios of Si:Al in the framework, especially ratios of 20:1 and higher. The premier example of such materials is silicalite, a crystalline silica polymorph as described in U.S. Pat. No. 4,061,724. The material designated as ZSM-5 (U.S. Pat. No. 3,702,886) and other members of this family, such as ZSM-12, which differ from ZSM-5 in pore size, are illustrative of other highly siliceous molecular sieves which may be used in the practice of our invention. See also, U.S. Pat. No. 4,257,885 for the preparation of analogous materials. The foregoing named molecular sieves must be clearly understood to be only representative of the class which is defined by silica tetrahedra in the framework and a limited number of alumina tetrahedra in the framework as defined by the silicon:aluminum atom ratio given above. This class of molecular sieves is hydrophobic, which is an important feature of the adsorbents used in our sorbent tubes.

High silica molecular sieves are not the sole class of zeolitic materials which may be used in the practice of our invention. In particular, both zeolites Y and L, especially dealuminated zeolites Y and L, and particularly the cation exchanged dealuminated materials, are effective in the practice of our invention. The particular cations preferred in the practice of our invention include the alkali metal and alkaline earth metal cations. Among the alkali metal cations the sodium and potassium cations, and especially the potassium cations, are favored in the practice of our invention. Of the alkaline earth metal cations the calcium and magnesium cations are preferred. The various aluminophosphates, as exemplified by AlPO-5, AlPO-41, and AlPO-11, also are effective as trap adsorbents. Other molecular sieves as trap adsorbents include zeolite omega (ZSM-4) and the ammonium form of ferrierite (ZSM-35). All of the foregoing are well known in the art and need not be elaborated upon further.

Although the foregoing class of zeolitic materials are the effective adsorbents in our invention it needs to be clearly understood from the outset that adsorbent products, whatever their form (i.e., spheres, pellets, extrudates, etc.) are aggregates of very small particles which typically are held together by a binder. Among materials commonly employed as binders for zeolitic materials are various clays, alumina, and silica. What we have found is that the nature of the binder can have important effects on the performance of the zeolitic materials; clays generally adversely affect performance, and silica is generally a preferred binder. Silica as a binder is excellent for potentially reactive analytes, and also works well for a broad range of analytes. Even though binder effects may be substantial and may determine whether a particular formulation is suitable in the practice of our invention, it needs to be clearly recognized and emphasized that binder effects are readily determined by simple experimentation; one skilled in the adsorbent art would easily be able to ascertain whether a binder was unsuitable and whether a particular formulation was successful in the practice of our invention.

The conditions under which our sorbent tubes are used in the purge and trap procedure include an adsorption cycle usually conducted at about ambient temperature. Certainly it is possible to cool the adsorbent, but generally adsorption is conducted without significant cooling of the sorbent tube. The desorption cycle is preferably conducted as at high a temperature as is feasible. High temperatures favor linear response, and since the materials of our invention are structurally thermostable desorption temperatures of 200°–400° C. are recommended. However, desorption may be performed over the range from about 50° up to 500° C., even though the aforementioned narrower temperature range encompasses the more usual working conditions. Excellent linearity in desorption among the members of a broad spectrum of organic materials is observed under these conditions.

Residual organic materials are removed from the molecular sieves by heating the latter to what is commonly called a bakeout temperature. The higher the bakeout temperature, the lower will be the residual organic materials on the adsorbent, since the desorption rate is an exponential function of the amount of organic material remaining on the adsorbent. Usually the bakeout temperature is substantially greater than the desorption temperature, and for the materials of our invention a bakeout temperature about 400° C. or higher is common. It is to be emphasized that high bakeout temperatures are integral to the absence of hysteresis and a minumum bakeout temperature of 350° C. is recommended. The maximum bakeout temperature will depend on the thermal stability of the molecular sieve utilized in the practice of this invention, a property which a skilled artisan can readily determine either from the prior art or by simple experimentation. Generally the maximum bakeout temperature will be at least 700° C., although additional benefits are unlikely above a bakeout temperature of 600° C.

Contrary to the adsorbents that are currently available, the molecular sieves used in the traps of our invention can eliminate or greatly reduce the dry purge step mandated by the EPA protocols, a step which is included there to reduce the amount of water on the adsorbent. Using a molecular sieve highly selective for water over organic compounds can remove the water prior to its contact with the adsorbent for volatile organic compounds. The water removing adsorbent can be included either as part of a unitary adsorption tube, with the water removing adsorbent placed prior to the second adsorbent, or as a separate bed. Having the water removing adsorbent present as a separate bed has the advantage of not only protecting the adsorbent for volatile organic compounds from moisture, so as to maximize its capacity for organic materials, but it also permits the bed to be removed from the desorption flow path, thereby keeping moisture from the chromatographic instrument. On the other hand, having the water removing adsorbent as the first bed in the adsorbent tube allows hydrophilic adsorbents to be used, but during the desorption step this water is sent into the chromatographic instrument. For most chromatographic detectors this does not pose a problem.

EXAMPLES

Preparation of materials. The following procedure is representative of those employed for dealumination of sieves and for preparation of extrudates of molecular sieves using a silica binder. Silicalite was prepared essentially as described in U.S. Pat. No. 4,061,724 and formed into extrudates using silica as a binder. Potassium-exchanged dealuminated L-zeolite was prepared as follows. L-zeolite used as a starting material at 17.0 weight percent alumina, 66.5 weight percent silica and 16.2% potassium oxide. Dealumination was performed by treating the potassium-exchanged L-zeolite with $K_2SiF_6$ at 95° C. to effect exchange of aluminum by silicon; see U.S. Pat. No. 4,836,911 and related patents cited therein. Proceeding essentially as described there afforded ultimately a potassium-exchanged dealuminated L-zeolite containing 9.0 weight percent alumina, 81.8 percent silica, and 8.1 percent potassium. A silica-bonded powder was made using approximately 4 parts of the dealuminated zeolite described above and 1 part by weight of silica (as a 50 weight percent aqueous suspension). The product was calcined at 550° C. for 1 hour as a final step of its preparation.

Adsorbent Evaluations; General Method. The 80 compounds of EPA method 524.2 rev 4 were used to evaluate adsorbents for purge and trap applications as 20 ppb solutions (5 mL total). The procedures mandated in the foregoing EPA method were rigorously followed in all details. 5 mL of the water standard was introduced into the sparge tube and sparged with helium at a flow rate of 40 mL/min. for 6 minutes. A 30 second dry purge then was initiated, after which the sample was desorbed into the gas chromatograph for 2 minutes.

Comparison of Carbon and a Dealuminated Y Zeolite/ Silicalite Combination. The performance of a porous carbon frequently used in purge and trap applications (Vocarb 3000™ from Supelco) was compared with that using a combination column consisting first of 0.25 grams silicalite followed by 0.35 grams dealuminated zeolite Y. Since both of these materials are hydrophobic it was unnecessary to use a water removing adsorbent prior to the dealuminated Y-silicalite combination. The dealuminated Y is available as HiSiv™ 1000 from UOP. The following conditions were used for the Vocarb™ 3000 trap: 6 minutes purge time, 0.5 minutes dry purge time, 250° C. desorb temperature, 2 minutes desorb time, 260° C. bake temperature, and 4 minutes bake time. The conditions used for the mixed silicalite/dealuminated Y trap were: 6 minutes purge time, 0.5 minutes dry purge time, 300° C. desorb temperature, 2 minutes desorb time, 350° C. bake temperature, and 4 minutes bake time.

Results are given in Tables 1 and 2, where RSD is the relative standard deviation. It is clear from the RSDs of the two adsorbents that the zeolitic adsorbent gives improved results by a factor of about 10!

Table 3 shows similar results for just the benzene-toluene-xylene (BTX) triad where the superiority of the zeolite is equally apparent. The porous carbon used here was BTEX- TRAP™ from Supelco. The dealuminated K-L trap used a prebed of 3A/4A as a water removing adsorbent in the adsorbent trap. The conditions for porous carbon included a 6 minute purge time, 0.5 minute dry purge time, 240° C. desorb temperature, 2 minutes desorb time, 250° C. bake temperature and 4 minutes bake time. Conditions for the dealuminated K-L included 6 minutes purge time, 0.5 minutes dry purge time, 300° C. desorb temperature, 2 minutes desorb time, 350° C. bake temperature and 4 minutes bake time.

TABLE 1

Analytical Results Using a Porous Carbon[a]

| NAME | MEAN | STD DEV | RSD |
|---|---|---|---|
| 1,1,1-trichlorethane | 1073003 | 7762.2889 | 0.7% |
| 1,1,2,2-tetrachloroethane | 1962280 | 14322.148 | 0.7% |
| 1,1,2-trichloroethane | 930511.3 | 22986.416 | 2.5% |
| 1,1,-dichloroethane | 1914072 | 42060.012 | 2.2% |
| 1,1-dichloroethene | 825721.3 | 3334.5351 | 0.4% |
| 1,2-dichlorobenzene | 2250716 | 47552.243 | 2.1% |
| 1,2-dichloroethane | 1214162 | 16783.63 | 1.4% |
| 1,2-cichloroethane-d-4-(Surr) | 2364683 | 50432.027 | 2.1% |
| 1,2-dichloropropane | 1349307 | 13825.936 | 1.0% |
| 1,3-dichlorobenzene | 2665244 | 40398.342 | 1.5% |
| 1,4-dichlorobenzene | 1843678 | 39785.442 | 2.2% |
| 1,4-difluorobenzene | 5231582 | 109530.66 | 2.1% |
| 2-butanone | 190286.3 | 17924.506 | 9.4% |
| 4-bromofluorobenzene (Surr) | 3377882 | 41234.618 | 1.2% |
| 4-methyl-2-pentanone | 2292253 | 128868.03 | 5.6% |
| acetone | 550060 | 57588.929 | 10.5% |
| benzene | 3310440 | 32726.564 | 1.0% |
| bromochloromethene | 856679.3 | 10872.856 | 1.3% |
| bromodichloromethane | 1603196 | 8444.2383 | 0.5% |
| bromoform | 1417580 | 9501.3682 | 0.7% |
| bromomethane | 601798 | 8255.0262 | 1.4% |
| carbon disulfide | 2660174 | 35866.976 | 1.3% |
| carbon tetrachloride | 984415.3 | 19730.34 | 2.0% |
| chlorobenzene | 1909578 | 8173.4593 | 0.4% |
| chlorobenzene-d-5 | 3971253 | 120106.72 | 3.0% |
| chloroethane | 575028.7 | 4752.8123 | 0.8% |
| chloroform | 1811608 | 16696.085 | 0.9% |
| chloromethane | 693610.3 | 13199.577 | 1.9% |
| cis-1,3-dichloropropene | 1667447 | 30941.095 | 1.9% |
| dibromochloromethane | 1036894 | 14717.073 | 1.4% |
| ethylbenzene | 992296.7 | 31598.304 | 3.2% |
| freon | 1290755 | 12830.517 | 1.0% |
| m,p-xylene | 2504470 | 70025.218 | 2.8% |
| methylene chloride | 916302.7 | 8591.0922 | 0.9% |
| o-xylene | 2096146 | 53071.211 | 2.5% |
| tetrachloroethene | 1259636 | 12529.492 | 1.0% |
| toluene | 3334355 | 20428.886 | 0.6% |
| toluene-d8 (Surr) | 6043642 | 85021.276 | 1.4% |
| trans-1,2-dichloroethene | 742714 | 1541.245 | 0.2% |
| trans-1,3-dichloropropene | 1356365 | 53663.814 | 4.0% |
| trichloroethene | 893467.7 | 21148.694 | 2.4% |
| trichlorofluoromethane | 1366822 | 34528.926 | 2.5% |
| vinyl acetate | 3676599 | 410714.13 | 11.2% |
| vinyl chloride | 830018.7 | 21656.355 | 2.6% |
| Average Deviation | | | 1.5% |

[a]Vocarb 3000 ™ from Supelco

TABLE 2

Analytical Results Using a Dealuminated Zeolite Y/Silicalite Combination.

| NAME | MEAN | STD DEV | RSD |
|---|---|---|---|
| 1,1,1-trichlorethane | 49.47322 | 0.05301 | 0.1% |
| 1,1,2,2-tetrachloroethane | 51.25270 | 0.13584 | 0.3% |
| 1,1,2-trichloroethane | 49.32806 | 0.29308 | 0.6% |
| 1,1,-dichloroethane | 51.25370 | 0.36042 | 0.7% |
| 1,1-dichloroethene | 51.26565 | 0.22267 | 0.4% |
| 1,2-dichlorobenzene | 47.71028 | 0.28867 | 0.6% |
| 1,2-dichloroethane | 49.65380 | 0.25778 | 0.5% |

TABLE 2-continued

Analytical Results Using a Dealuminated Zeolite Y/Silicalite Combination.

| NAME | MEAN | STD DEV | RSD |
|---|---|---|---|
| 1,2-cichloroethane-d-4-(Surr) | 55.48516 | 0.54709 | 1.0% |
| 1,2-dichloropropane | 50.86661 | 0.53193 | 1.0% |
| 1,3-dichlorobenzene | 48.48012 | 0.38769 | 0.8% |
| 1,4-dichlorobenzene | 46.52400 | 0.26441 | 0.6% |
| 1,4-difluorobenzene | 50 | 0 | 0.0% |
| 2-butanone | 48.60923 | 0.32230 | 0.7% |
| 4-bromofluorobenzene (Surr) | 50.35030 | 0.39093 | 0.8% |
| 4-methyl-2-pentanone | 45.28939 | 0.20616 | 0.5% |
| acetone | 45.78187 | 0.24407 | 0.5% |
| benzene | 50.56647 | 0.29435 | 0.6% |
| bromochloromethene | 50 | 0 | 0.0% |
| bromodichloromethane | 49.41622 | 0.41872 | 0.8% |
| bromoform | 48.17718 | 0.16021 | 0.3% |
| bromomethane | 49.70859 | 0.58573 | 1.2% |
| carbon disulfide | 49.44925 | 0.37802 | 0.8% |
| carbon tetrachloride | 48.34961 | 0.44612 | 0.9% |
| chlorobenzene | 49.48621 | 0.23345 | 0.5% |
| chlorobenzene-d-5 | 50 | 0 | 0% |
| chloroethane | 48.81300 | 0.12865 | 0.3% |
| chloroform | 50.70420 | 0.23126 | 0.5% |
| chloromethane | 51.51909 | 0.31144 | 0.6% |
| cis-1,3-dichloropropene | 49.50070 | 0.23642 | 0.5% |
| dibromochloromethane | 49.22760 | 0.10561 | 0.2% |
| ethylbenzene | 40.62301 | 0.30415 | 0.7% |
| freon | 49.39019 | 0.39037 | 0.8% |
| m,p-xylene | 47.66033 | 0.15059 | 0.3% |
| methylene chloride | 50.39898 | 0.17219 | 0.3% |
| o-xylene | 48.66629 | 0.24089 | 0.5% |
| tetrachloroethene | 45.67357 | 0.19136 | 0.4% |
| toluene | 48.59965 | 0.30111 | 0.6% |
| toluene-d8 (Surr) | 56.38251 | 0.26181 | 0.5% |
| trans-1,2-dichloroethene | 50.78398 | 0.26817 | 0.5% |
| trans-1,3-dichloropropene | 49.35186 | 0.23636 | 0.5% |
| trichloroethene | 46.28359 | 0.24138 | 0.5% |
| trichlorofluoromethane | 50.18067 | 0.19185 | 0.4% |
| vinyl acetate | 63.63098 | 0.37509 | 0.6%1 |
| vinyl chloride | 51.67100 | 0.27348 | 0.5% |
| Average Deviation | | | 0.2% |

TABLE 3

Performance of a Dealuminated Zeolite L for BTX Analysis[a]

| Dealuminated Zeolite L | Average | STD | Relative STD |
|---|---|---|---|
| Benzene | 15434.67 | 155.6031 | 1.008140513 |
| Toluene | 24477 | 61.21274 | 0.250082705 |
| Ethylbenzene | 23665.33 | 15.04438 | 0.063571379 |
| Para-xylene | 42792 | 444.5301 | 1.038815874 |
| Meta-xylene | 25623 | 81.95731 | 0.319858354 |
| Ortho-xylene | 24088.67 | 341.9186 | 1.419416903 |
| Supelco BTX trap | | | |
| Benzene | 12312.33 | 361.1016 | 2.932844211 |
| Toluene | 22548.33 | 1335.725 | 5.923832046 |
| Ethylbenzene | 21555 | 1172.638 | 5.440215625 |
| Para-xylene | 40985 | 2511.592 | 6.128074972 |
| Meta-xylene | 23559 | 1388.298 | 5.892857247 |
| Ortho-xylene | 22312.67 | 1309.732 | 5.869902503 |

[a]BTX is the commonly used abbreviation for benzene, toluene, and aromatic C-8 (ethylbenzene and the 3 isomeric xylenes.)

What is claimed is:

1. A method of sequential adsorption, storage, and desorption of a multiplicity of organic compounds contained in a gas stream, where each of said organic compounds is present at a concentration from about 0.5 parts per billion to about 100 parts per million with a proportion determined by the ratio of its concentration to the total concentration of all organic compounds, said method retaining the proportions of each of said organic compounds in each of adsorption, storage, and desorption comprising flowing said gas stream through an adsorbent bed of a molecular sieve to adsorb said organic compounds in amounts having the same proportion as each are found in said gas stream, storing the adsorbed organic compounds in the adsorbent bed, desorbing said organic compounds at a temperature between about 50° and about 500° C. in substantially the same proportion as each are stored in said adsorbent bed, and removing all residual organic compounds from the adsorbent bed by heating said adsorbent bed in a flowing gas at a temperature of at least 350°C.

2. The method of claim 1 where the molecular sieve is selected from the group consisting of: siliceous molecular sieves having a framework ratio of silicon to aluminum atoms of at least 20:1; cation-exchanged zeolites Y and L, and dealuminated zeolites Y and L; zeolite omega; ammonium-exchanged ferrierite; aluminophosphates; and combinations thereof.

3. The method of claim 2 where the molecular sieve is a siliceous molecular sieve having a framework ratio of silicon to aluminum atoms of at least 20:1.

4. The method of claim 3 where the molecular sieve is silicalite, ZSM-5, ZSM-12, and combinations thereof.

5. The method of claim 2 where the molecular sieve is a cation-exchanged zeolite Y or zeolite L, or a dealuminated zeolite Y or L, and the cation is selected from the group consisting of alkali and alkaline earth metal cation.

6. The method of claim 5 where the cation is an alkali metal cation.

7. The method of claim 6 where the alkali metal cation is a sodium or potassium cation.

8. The method of claim 7 where the alkali metal cation is potassium cation.

9. The method of claim 5 where the cation is an alkaline earth metal cation.

10. The method of claim 9 where the alkaline earth metal cation is calcium or magnesium cation.

11. The method of claim 1 further characterized in having a water removing adsorbent placed prior to the said molecular sieve adsorbent bed.

12. In the method of analyzing organic materials in air or water by concentrating said organic materials using a purge and trap procedure where a gas stream containing said organic materials flows through a sorbent tube containing an adsorbent bed which removes said organic materials from the gas stream and retains said organic materials in the adsorbent bed, the improvement wherein the sorbent tube contains a molecular sieve as the adsorbent bed.

13. The method of claim 12 where the molecular sieve is selected from the group consisting of: siliceous molecular sieves having a framework ratio of silicon to aluminum atoms of at least 20:1; cation-exchanged zeolites Y and L, and dealuminated zeolites Y and L; zeolite omega; ammonium-exchanged ferrierite; aluminophosphates; and combinations thereof.

14. The method of claim 13 where the molecular sieve is a siliceous molecular sieve having a framework ratio of silicon to aluminum atoms of at least 20:1.

15. The method of claim 14 where the molecular sieve is silicalite, ZSM-5.ZSM-12, and combinations thereof.

16. The method of claim 13 where the molecular sieve is a cation-exchanged zeolite Y or zeolite L, or a dealuminated zeolite Y or L, and the cation is selected from the group consisting of alkali and alkaline earth metal cation.

17. The method of claim 16 where the cation is an alkali metal cation.

18. The method of claim 17 where the alkali metal cation is a sodium or potassium cation.

19. The method of claim 18 where the alkali metal cation is potassium cation.

20. The method of claim 16 where the cation is an alkaline earth metal cation.

21. The method of claim 20 where the alkaline earth metal cation is calcium or magnesium cation.

22. The method of claim 12 further characterized in having a water removing adsorbent placed prior to the said molecular sieve adsorbent bed.

\* \* \* \* \*